US00PP22605P2

(12) United States Plant Patent
Slaughter et al.

(10) Patent No.: US PP22,605 P2
(45) Date of Patent: Mar. 27, 2012

(54) PEACH TREE, 'BURPEACHTWENTYFIVE'

(50) Latin Name: *Prunus persica*
Varietal Denomination: Burpeachtwentyfive

(75) Inventors: John K. Slaughter, Fresno, CA (US); Timothy J. Gerdts, Kingsburg, CA (US)

(73) Assignee: The Burchell Nursery, Inc., Oakdale, CA (US)

( * ) Notice: Subject to any disclaimer, the term of this patent is extended or adjusted under 35 U.S.C. 154(b) by 0 days.

(21) Appl. No.: 12/925,327

(22) Filed: Oct. 18, 2010

(51) Int. Cl.
*A01H 5/00* (2006.01)

(52) U.S. Cl. ..... Plt./194

(58) Field of Classification Search ..... Plt./194
See application file for complete search history.

*Primary Examiner* — Annette Para

(74) *Attorney, Agent, or Firm* — Paine Hamblen, LLP

(57) ABSTRACT

A new and distinct variety of peach tree (*Prunus persica*), which is denominated varietally as 'Burpeachtwentyfive', and which produces an attractively colored red-fleshed, clingstone peach which is mature for harvesting and shipment approximately May 8 to May 13 under the ecological conditions prevailing in the San Joaquin Valley of central California.

4 Drawing Sheets

Latin name of the genus and species of the plant claimed:

BACKGROUND OF THE NEW VARIETY

The present invention relates to a new, novel, and distinct variety of peach tree, *Prunus persica* and which has been denominated varietally as 'Burpeachtwentyfive'.

ORIGIN

The present variety of peach tree resulted from an on-going program of fruit and nut tree breeding. The purpose of this program is to improve the commercial quality of deciduous fruit and nut varieties, and rootstocks, by creating and releasing promising selections of prunus, malus and regia species. To this end we make both controlled and hybrid cross pollinations each year in order to produce seedling populations from which improved progenies are evaluated and selected.

The seedling, 'Burpeachtwentyfive' was originated by us and selected from a population of seedlings growing in our experimental orchards located near Fowler, Calif. The seedlings, grown on their own roots, were derived from a cross that we made in 2002 of the peach which was then identified as J40.110 and later patented as 'Burpeachtwentytwo' peach tree (U.S. Plant Pat. No. 17,258). 'Burpeachtwentytwo' is considered to be an early ripening, yellow-fleshed, clingstone peach tree, and was used as the seed parent. Further, an un-named, unpatented early ripening yellow-fleshed peach tree was used as the pollen parent. As the fruit ripened the resulting seed from this cross, which were too immature to retrieve conventionally were embryo cultured, in vitro, and then subsequently grown in a greenhouse to an appropriate development stage. Subsequently, the new plants were field planted and grown for further evaluation. One seedling which is the present variety, exhibited especially desirable characteristics, and was then designated as 'N26.033'. This seedling was marked for subsequent observation. After the 2007 fruiting season, the new variety of peach tree 'N26.033', now 'Burpeachtwentyfive' was selected for advanced evaluation and repropagation.

ASEXUAL REPRODUCTION

Asexual reproduction of this new and distinct variety of peach tree was accomplished by budding the new peach tree 'N26.033' onto 'Nemaguard' Rootstock (un-patented). This was performed by us in our experimental orchard which is located near Fowler, Calif. Subsequent evaluations of these asexually reproduced plants have shown those asexual reproductions run true to the original tree. All characteristics of the original tree, and its fruit, were established, and appear to be transmitted through these succeeding asexual propagations.

SUMMARY OF THE VARIETY

'Burpeachtwentyfive' is a new and distinct variety of peach tree, which is considered of medium, to medium small size, and which has a moderate growth characteristic. This new peach tree is also a regular and productive bearer of relatively large, firm, red-fleshed, clingstone fruit which have a good flavor and eating qualities. This new peach tree has a relatively low chilling requirement of approximately 250 hours, and further produces relatively uniformly sized fruit throughout the tree. In addition to the foregoing, the fruit of the new peach tree also appears to have good handling and shipping qualities.

The 'Burpeachtwentyfive' peach tree bears fruit which are ripe for commercial harvesting and shipment on approximately May 5 to May 13 under the ecological conditions prevailing in the San Joaquin Valley of central California. In relative comparison to the 'Burpeachfourteen' peach tree (U.S. Pat. No. 14,342), which produces fruit having a similar harvesting date, the new variety of peach tree bears fruit which exhibits a more extensive red flesh color than the 'Burpeachfourteen' when both varieties have been grown and evaluated under the same cultural conditions, and at the same geographical location. Further, in comparison to U.S. Plant Pat. No. 17,258 from which the present variety was derived as a seed parent, the new peach tree variety is distinguishable by producing fruit which are ripe for harvesting at least as early as 5 days before that of U.S. Plant Pat. No. 17,258.

BRIEF DESCRIPTION OF THE DRAWINGS

The accompanying drawings, which are provided, are color photographs of the new peach tree variety.

Figure 1:
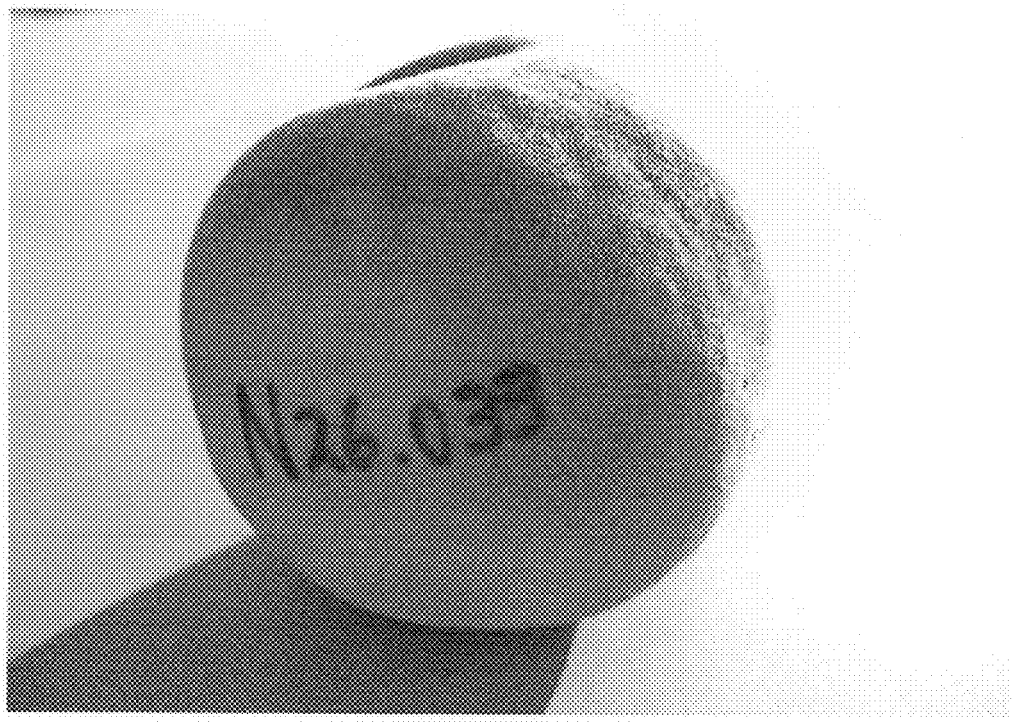
FIG. 1 depicts a whole mature fruit (labeled 'N26.033'), and which is sufficiently matured for harvesting and shipment.

The colors in these photographs are as nearly true as is reasonably possible in a color representation of this type. Due to chemical development, processing and printing, the leaves and fruit depicted in these photographs may, or may not, be accurate when compared to the actual specimen. For this reason, future color references should be made to the color plates (Royal Horticultural Society) and descriptions provided, hereinafter.

NOT A COMMERCIAL WARRANTY

The following detailed description has been prepared to solely comply with the provisions of 35 U.S.C. §112, and does not constitute a commercial warranty, (either expressed or implied), that the present variety will in the future display the botanical, pomological or other characteristics as set forth, hereinafter. Therefore, this disclosure may not be relied upon to support any future legal claims, including, but not limited to, breach of warranty of merchantability, or fitness for any particular purpose, or non-infringement which is directed, in whole, or part, to the present variety.

DETAILED DESCRIPTION

Referring more specifically to the pomological details of this new and distinct variety of peach tree, the following has been observed during the sixth fruiting season under the ecological conditions prevailing at the orchards of the assignee which are located near the town of Fowler, county of Fresno, state of California. All major color code designations are by reference to The R.H.S. Colour Chart (Fourth Edition) provided by The Royal Horticultural Society of Great Britain. Common color names are also occasionally used.

TREE

*Size.*—Generally. Considered medium to medium small as compared to other common commercial peach cultivars ripening in the early season of maturity. The tree of the present variety was pruned to a height of approximately 220.0 cm to about 255.0 cm at commercial maturity.

*Vigor.*—Considered vigorous. The present peach tree variety grew from about 140.0 cm to about 145.0 cm in height during the first growing season. The new variety was pruned to a height of approximately 140.0 cm during the first dormant season, and primary scaffolds were then selected for the desired tree structure.

*Productivity.*—Productive. Fruit set varies from more than the desired crop load to levels at or slightly below desired levels. The fruit set is spaced by thinning to develop the remaining fruit into the desired market-sized fruit. The number of the fruit set varies with the prevailing climatic conditions; proximity to adjacent varieties; bee activity; and prevailing cultural practices employed during the bloom period. Therefore, productivity is not a distinctive characteristic of the new variety.

*Fruit bearing.*—Regular. Fruit set has been acceptable during the previous years of observation, and thinning was necessary during the past 5 years on both the original seedling and on subsequent asexually produced trees.

*Form.*—Upright, and pruned into a vase shape.

*Density.*—Considered moderately dense. It has been discovered that pruning the branches from the center of the tree to obtain a resulting vase shape allows for air movement and appropriate amounts of sunlight to enhance fruit color, and renewal of fruiting wood throughout the tree.

*Hardiness.*—The present tree was grown and evaluated in USDA Hardiness Zone 9. The calculated winter chilling requirements of the new tree is approximately 250 hours at a temperature below 7.0 degrees C. The present variety appears to be hardy under typical central San Joaquin Valley climatic conditions. In view of its lower chilling requirement the present variety of peach tree appears that it could be suitably grown in climatic zones that have fewer chilling hours than that of USDA Hardiness Zone 9. Testing to verify this suitability of the variety has not been undertaken by the inventors.

TRUNK

*Diameter.*—Approximately 9.5 cm in diameter when measured at a distance of approximately 15.24 cm above the soil level. This measurement was taken at the end of the fifth growing season.

*Bark texture.*—Considered moderately rough, with numerous folds of papery scarfskin being present.

*Lenticels.*—Numerous flat, oval lenticels are present. The lenticels range in size from approximately 4.0 millimeters to about 6.5 mm in width, and between about 1.0 and about 2.0 millimeters in height. The development and size of the trunk lenticels can be influenced by the ambient growing conditions and are not, necessarily, a dependable characteristic of this variety.

*Lenticel color.*—Considered an orange brown, (RHS Greyed-Yellow Group 162 A).

*Bark coloration.*—Variable, but it is generally considered to be a medium brown, (RHS Greyed-Orange Group 166 B). This bark description was taken from trees in their fifth leaf which have not yet ruptured the scarf skin, nor developed bark furrowing which is much more typical of the bark of older trees.

BRANCHES

*Size.*—Considered medium for the variety.

*Diameter.*—Average as compared to other peach varieties. The branches have a diameter of about 6.5 centimeters when measured during the fifth year after grafting.

*Surface texture.*—Average, and appearing furrowed on wood which is several years old.

*Crotch angles.*—Primary branches are considered variable, and are usually growing at an angle of about 53 to about 59 degrees when measured from a horizontal plane. This particular characteristic is not considered distinctive of the variety as this characteristic can be influenced, to some degree, by tree vigor, rootstock and other cultural conditions.

*Current season shoots.*—Surface texture — Substantially glabrous.

*Internode length.*—Approximately 2.5 cm.

*Color of mature branches.*—Grey brown, (RHS Grey-Brown Group 199 D).

*Current seasons shoots.*—Color. — Light green, (RHS Yellow-Green Group 144 B). The color of new shoot tips is considered a bright and shiny green (RHS Green Group 143 C). The vegetative shoot color can be significantly influenced by plant nutrition, irrigation practices and exposure to sunlight, and therefore should not be considered a consistent botanical characteristic.

LEAVES

*Size.*—Considered medium for the species. Leaf measurements have been taken from vigorous, upright, current-season growth at approximately mid-shoot. It should be understood that the leaf size is often influenced by prevailing growing conditions, quality of sunlight, and the location of the leaf within the tree canopy. For this reason, leaf sizes can vary significantly based upon the factors listed above and are not typically considered a dependable botanical descriptor.

*Leaf length.*—Approximately 155.0 to about 170.0 millimeters.

*Leaf width.*—Approximately 28.0 to about 33.0 millimeters.

*Leaf base-shape.*—The leaves generally exhibit equal marginal symmetry relative to the leaf longitudinal axis.

*Leaf form.*—Lanceolate. The leaves often exhibit a curvate growth pattern. This is particularly noticeable in the posterior ⅓ of the leaf. This growth pattern would include the mid-rib. The leaves typically display a dextrorsum growth expression when viewed from the ventral side thereof.

*Leaf tip form.*—Acuminate.

*Leaf color.*—Upper Leaf Surface — Dark green, (approximately RHS Green Group 138 A).

*Leaf texture.*—Glabrous.

*Leaf Color.*—Lower Surface — Deep green, (approximately RHS Green Group 143 B).

*Leaf venation.*—Pinnately veined.

*Mid-vein.*—Color. — Considered a light yellow-green, (approximately RHS Yellow-Green Group 150 D) in the early to mid period of the growing season.

*Leaf margins.*—Slightly undulating. Form. — Considered bluntly serrate, occasionally biserrate. Uniformity. — Considered generally uniform.

*Leaf petioles.*—Form. — Considered canaliculate but having a shallow channel and more pronounced trough. Size. — Considered medium small for the species. Length. — About 9.0 to about 11.0 mm. Diameter. — About 1.5 to about 2.0 mm. Color. — Pale green, (approximately RHS Yellow-Green Group N144 D).

*Leaf glands.*—Size. — Considered small for the species; approximately 1.0 mm in length, and about 1.0 mm in height. Number. — Generally one gland per marginal side is found. Occasionally two, and more rarely more than two glands per marginal side are found. Type. — Generally considered to be a tight, small reniform shaped gland. Color. — Considered a pale green, approximately (RHS Green Group 138 B).

*Leaf Stipules.*—Size. — Medium large for the variety. Number. — Typically 2 per leaf bud, and up to 6 per shoot tip. Form. — Lanceolate in form and having a serrated marginal edge. Color. — Green, (approximately RHS Green Group 137 B) when young, but graduating to a brown color, (approximately RHS Greyed-Orange group 174 C) with advancing senescence. The leaf stipules are considered to be early deciduous.

FLOWERS

*Flower buds.*—Generally — Depending upon the stage of development, the flower buds are approximately 5.0 millimeters wide; about 10.0 millimeters long; conic in form; and slightly appressed relative to the bearing shoot.

*Flower buds.*—Color — This characteristic is somewhat dependent upon the proximity to the bloom. The bud scales are deep purple, (approximately RHS Greyed-Purple Group 183 C). The flower buds are considered hardy under typical central San Joaquin Valley climatic conditions.

*Hardiness.*—No winter injury (bud death) has been noted during the last several years of observation in the central San Joaquin Valley. The new variety of peach tree has not been intentionally subjected to drought or heat stress, and therefore this information is not available.

*Date of first bloom.*—Observed on Feb. 8, 2010.

*Blooming time.*—Considered early in relative comparison to other commercial peach cultivars grown in the central San Joaquin Valley. The date of full bloom was observed on Feb. 13, 2010. The date of full bloom varies slightly with climatic conditions, and prevailing cultural practices.

*Duration of bloom.*—Approximately 9 days. This characteristic varies slightly with the prevailing climatic conditions.

*Flower type.*—The variety is considered to have a showy type flower.

*Flower size.*—The flower diameter at full bloom is approximately 46.0 to about 59.0 millimeters.

*Bloom quantity.*—Considered abundant.

*Flower bud frequency.*—Normally two flower buds appear per node, occasionally one, rarely more than two.

*Petal size.*—Generally — Considered large for the species. Length. — Approximately 24.0 mm. to about 29.0 mm. Width. — Approximately 20.0 mm. to about 24.0 mm.

*Petal form.*—Considered broadly ovate.

*Petal count.*—Nearly always 5.

*Petal texture.*—Glabrous.

*Petal color.*—Light pink, (approximately RHS Red-Purple Group 69 A) to a medium pink, (approximately RHS Red-Purple Group 70 D).

*Fragrance.*—Slight.

*Petal claw.*—Form. — The claw is considered generally ovoid. Length. — Approximately 8.0 to about 14.0 millimeters. Width. — Approximately 7.0 to about 11.0 millimeters.

*Petal margins.*—Generally — Considered variable, from nearly smooth to slightly ruffled, and moderately undulate.

*Petal apex.*—Generally considered gently acute or pointed. The petal apices generally exhibit a slight extended but rounded tip.

*Flower pedicel.*—Length. — Considered long, and having an average length of approximately 7.0 to about 9.0 millimeters. Diameter. — Considered average, approximately 2.0 millimeters. Color. — A medium brown, (approximately RHS Grey-Brown Group N199 C).

*Floral nectaries.*—Color. — A dull orange brown, (approximately RHS Greyed-Orange Group N167 C).

*Calyx.*—Surface Texture. — Generally considered glaborous. Color. — A dull purple, (approximately RHS Greyed-Red Group 181 C).

*Sepals.*—Surface Texture. — The surface of the sepals have a short, fine pubescent texture. Size. — Average, and ovate in form. Color. — A dull red, (approximately RHS Greyed-Orange Group 176 B).

*Anthers.*—Generally. — Average to small in length. Color. — Yellow (RHS Yellow-White Group 158 B).

*Pollen Production.*—Not abundant. The pollen has a yellow color, (approximately RHS Yellow Group 11 B).

*Fertility.*—A pollinator is typically-required.

*Filaments.*—Size. — Length is variable, approximately 13.0 to about 17.0 millimeters long. Color. — Considered white, (approximately RHS White Group 155 C).

*Pistil.*—Number. — Usually one, occasionally two, rarely more than two. Generally. — Average in size. Length. — Approximately 17.0 to about 22.0 millimeters including the ovary. Color. — Considered a very pale green, (approximately RHS Yellow-Green Group 145 D). Surface texture. — The variety has a long pubescent pistil.

FRUIT

*Maturity when described.*—Firm ripe condition (shipping ripe).

*Date of first picking.*—May 8, 2009. Date of last picking. — May 15, 2009. The date of harvest varies slightly with the prevailing climatic conditions and cultural practices.

*Size.*—Generally — Considered large, and uniform for the early date of maturity.

*Average cheek diameter.*—Approximately 63.0 to about 69.0 millimeters.

*Average axial diameter.*—Approximately 64.0 to about 72.0 millimeters.

*Typical weight.*—Approximately 202.0 grams. This characteristic is quite dependent upon the prevailing cultural practices, and therefore is not particularly distinctive of the new variety.

*Fruit form.*—Generally — Considered rounded to slightly oblate. The fruit is generally uniform in symmetry. It should be noted that occasional asymmetry can occur in the axial hemispheres of the fruit.

*Fruit suture.*—The suture along the fruit's margin can exhibit a broad shallow grooving or depression. No apparent callousing or stitching exists along the suture line.

*Suture.*—Color — Generally blushed to the same degree as the skin, (approximately RHS Red Group 46 D).

*Ventral surface.*—Form — Even and uniform in appearance when viewed in the direction of the stem cavity. Occasional creasing is noted at the ventral portion of the shoulder.

*Apex.*—Generally — Rounded.

*Base.*—Shape — Gently retuse.

*Stem cavity.*—Generally — Rounded and uniform in shape. The average depth of the stem cavity is about 5.0 mm. Average width of the stem cavity is about 8.0 mm.

*Fruit skin.*—Thickness. — Considered medium in thickness, and tenacious to the flesh. Surface Texture. — Short, fine and pubescent. The pubescence is moderately abundant. Taste. — Non-astringent. Tendency to crack. — Not observed in the previous years of evaluation.

*Fruit skin color.*—Blush Color. — Generally speaking, a red blush exists on a majority of the skin of the fruit (approximately RHS Red Group 46 D), and is typically more present on the portions of the fruit facing the sunlight. The blush covers approximately 80-90% of the fruit skin surface. The percentage of the blush on the fruit skin surface can vary, and is generally dependent upon the fruit's exposure to direct sunlight; specific fruit maturity; and also the prevailing ecological and cultural conditions under which the fruit is grown. Ground Color. — Yellow, (approximately RHS Yellow-Orange Group 18 A). The ground color of the fruit can vary significantly based upon the maturity of the fruit when this measurement is taken.

*Fruit stem.*—Size — Medium in length, approximately 6.0 to about 8.0 millimeters. Diameter. — Approximately 2.0 to about 3.0 millimeters. Color. — Pale yellow-green, (approximately RHS Yellow-Green Group N144 C).

Figure 2:
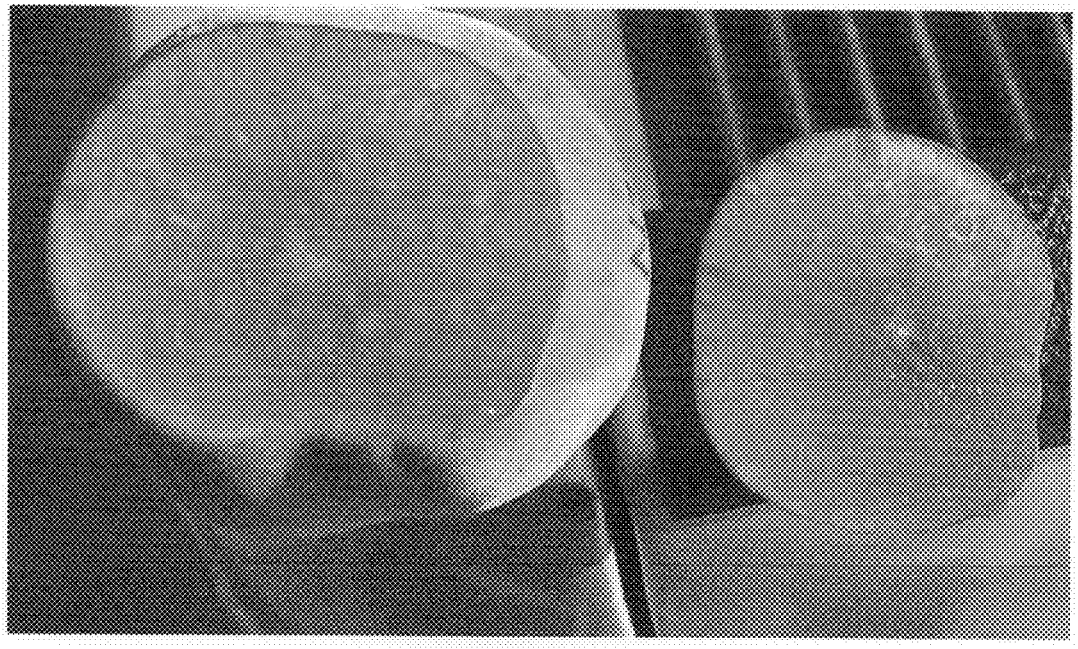
FIG. 2 shows a mature fruit which has been dissected sagitally along the mid-lateral plane, and which reveals the flesh characteristics thereof. The external and internal coloration of the fruit as shown in FIG. 2 is sufficiently matured for harvesting and shipment.
Figure 3:
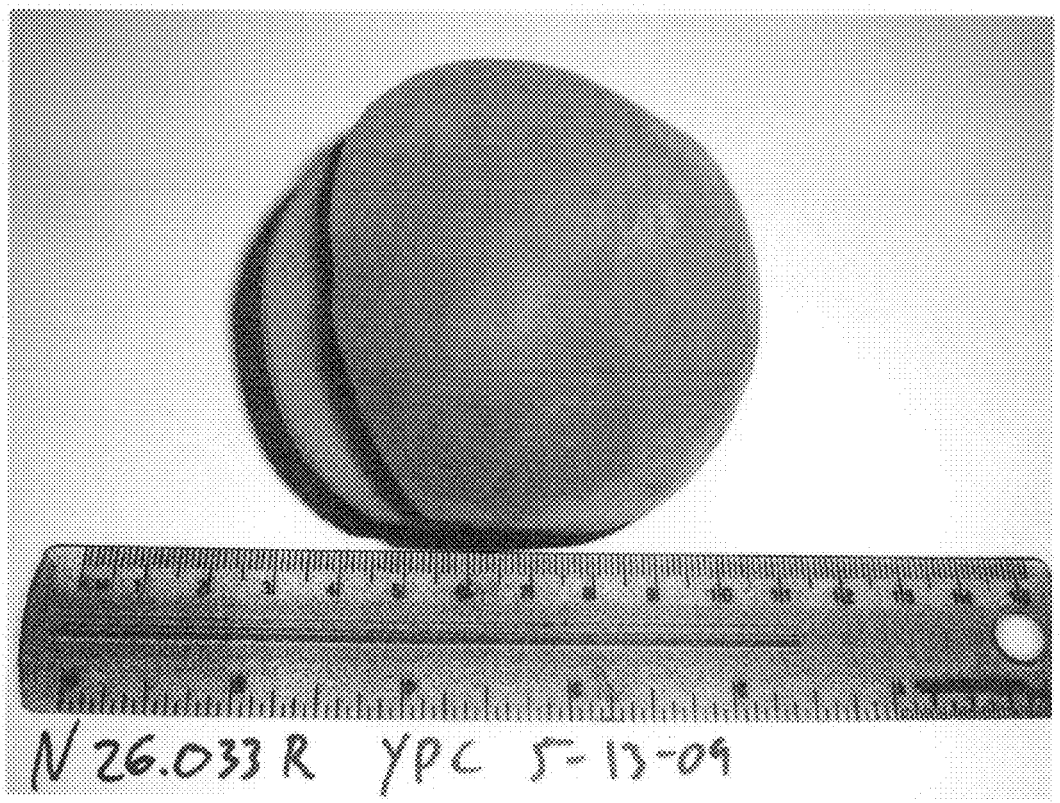
FIG. 3 shows the fruit of the present variety placed above a 15.0 cm metric ruler and which shows the approximate dimensions of the fruit and further illustrates the skin and background color patterns of the fruit.
Figure 4:
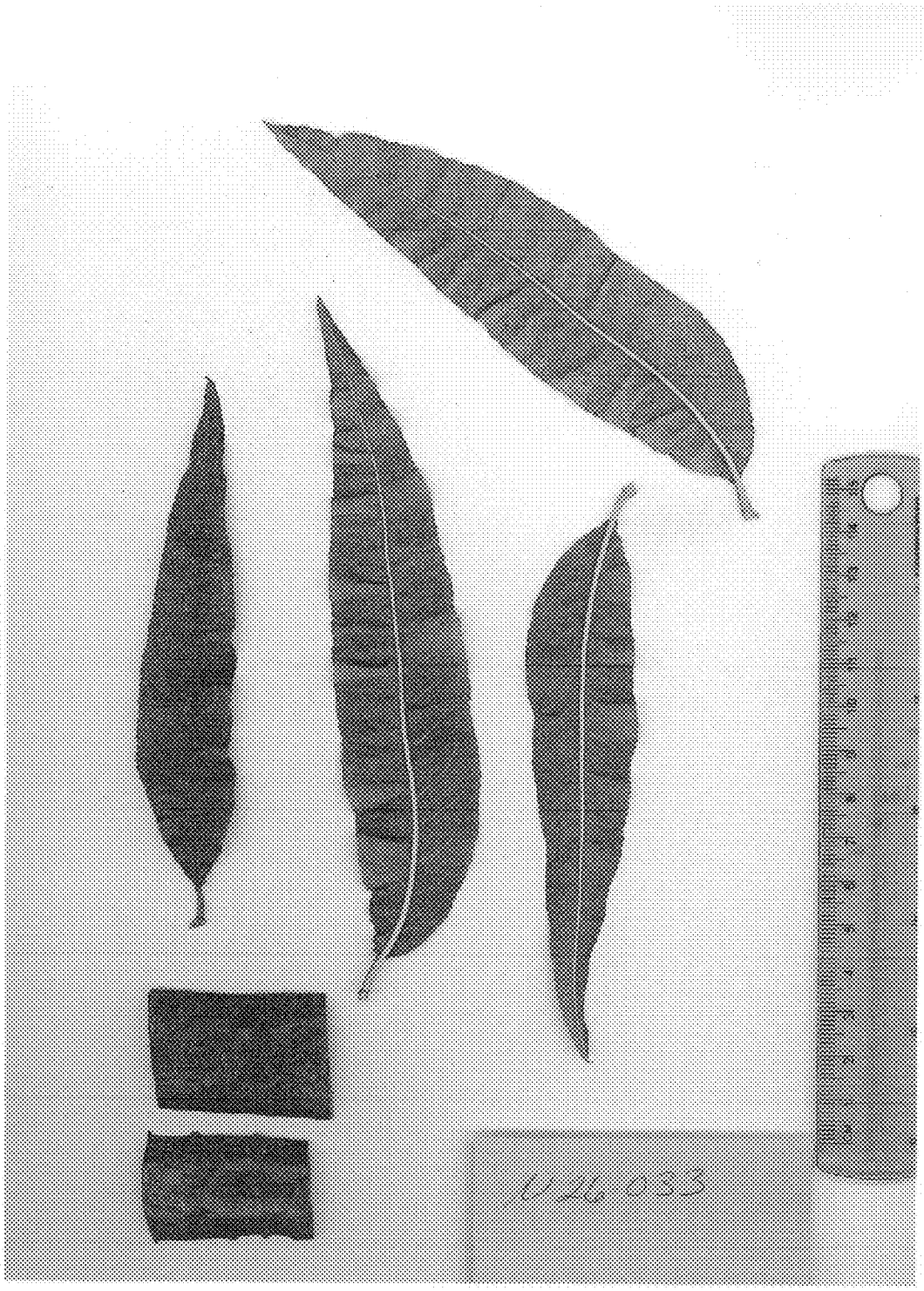
FIG. 4 shows 4 typical leaves and 2 separate pieces of trunk bark from the current variety.

*Fruit flesh.*—Ripening. — Considered even. Texture. — Firm, juicy and dense. Considered non-melting. Fibers. — Few are found. Aroma. — Slight. Eating Quality. — Considered very good. Flavor. — Considered sweet and with moderate acidity. The flavor is considered both pleasant and balanced. Juice Production. — Moderate. Brix. — About 13.0 to 18.0 degrees. This characteristic varies slightly with the number of fruit per tree; maturity of fruit when harvested; prevailing cultural practices; and the surrounding climatic conditions. Flesh Color. — Is considered a mixture of red, (approximately RHS. Red Group 43 A) and orange-yellow, (approximately RHS Yellow-Orange 23 B). The flesh color of the present variety generally increases in the reddish hue as the fruit approaches harvest maturity as seen in the photographs as provided with the present application (FIG. 2).

STONE

*Type.*—Clingstone.

*Size.*—Considered medium-large for the variety. The stone size varies significantly depending upon the tree vigor, crop load and prevailing growing conditions.

*Length.*—Average, about 28.0 to about 32.0 millimeters.

*Width.*—Average, about 21.0 to about 24.0 millimeters.

*Diameter.*—Average, about 15.0 to about 18.0 millimeters.

*Form.*—Ovoid.

*Base.*—The stone is usually rounded and considered narrow or slightly elongated relative to the general shape.

*Apex.*—Shape. — The stone apex is slightly lobed.

*Stone surface.*—Surface Texture — Generally speaking, the stone of the present variety is considered fragile and does not have sufficient time to develop and mature when compared to the stones of more medium or later season ripening varieties. Therefore, the stone is lighter in color, more porous, and less dense than stones of medium and late season varieties which have had more time to develop, harden and lignify. Surface pitting is generally more noted toward the dorsal edges of the stone. Ridges. — Ridging is generally more prominent and is usually oriented parallel and laterally relative to the ventral margin. Ventral Edge. — The ventral edge is generally considered moderately smooth. Dorsal Edge. — Shape — Generally considered moderately rough and uneven. The folds of the surface ridges appearing on the external margins often end abruptly along the external margin of the dorsal surface creating an irregular edge.

*Stone Color.*—The color of the dry stone is generally considered a pale yellow-white, (approximately Yellow Group RHS 12 C). This depends, to some degree, on the moisture content of the stone. This color is variable however, and may also be affected by oxidation. In view of this variability, this color characteristic cannot be considered distinctive of the new variety.

*Tendency to split.*—Splitting has occasionally been noted.

*Kernel.*—Size. — The kernel is considered medium-small in size. Form. — Considered generally ovoid but as the immature embryo and its cotyledons have not fully developed, the kernel form generally appears as shriveled and underdeveloped especially on the basal end. Pellicle. — Slightly pubescent. Color. — (RHS Yellow-Orange Group 19 D).

*Use.*—The present variety 'Burpeachtwentyfive' is considered to be a peach tree of the early season of maturity, and which produces fruit which are considered to be firm, attractively colored, and which are useful for both local and long distance shipping.

*Keeping quality.*—Appears excellent. The fruit of the present variety has stored well for up to 30 days after harvest at 1.0 degree Celsius.

*Shipping quality.*—Good. The fruit of the new peach tree variety showed minimal bruising of flesh or skin damage after being subjected to normal harvesting and packing procedures.

*Resistance to insects and disease.*—No particular susceptibilities were noted. The present variety has not been tested to expose or detect any susceptibilities or resistances to any known plant and/or fruit diseases.

Although the new variety of peach tree possesses the described characteristics when grown under the ecological conditions prevailing near Fowler, Calif., in the Central part of the San Joaquin Valley of California, it should be understood that variations of the usual magnitude and characteristics incident to changes in growing conditions, fertilization, pruning, pest control, frost, climatic variables and horticultural management are to be expected.

Having thus described and illustrated our new variety of peach tree, what we claim is new, and desire to secure by Plant Letters Patent is:

1. A new distinct variety of peach tree, substantially as illustrated and described, and which is characterized principally as to novelty by producing an attractively colored red-fleshed, clingstone peach which is mature for harvesting and shipment approximately May 8 to May 13 under the ecological conditions prevailing in the San Joaquin Valley of central California.

* * * * *